United States Patent [19]

Fladda

[11] Patent Number: 5,245,200
[45] Date of Patent: Sep. 14, 1993

[54] APPARATUS AND METHOD FOR PREVENTING BLOCKAGE OF A MEASURING HEAD FOR EFFECTING MEASUREMENTS OF SUSPENDED SUBSTANCES

[76] Inventor: Gerdt H. Fladda, Djursholmsvägen 88, S-183 51 Täby, Sweden

[21] Appl. No.: 807,851
[22] PCT Filed: Apr. 2, 1990
[86] PCT No.: PCT/SE90/00212
 § 371 Date: Jan. 10, 1992
 § 102(e) Date: Jan. 10, 1992
[87] PCT Pub. No.: WO91/00993
 PCT Pub. Date: Jan. 24, 1991

[30] Foreign Application Priority Data

Jul. 10, 1989 [SE] Sweden .............................. 8902485
Jul. 10, 1989 [SE] Sweden .............................. 8902486

[51] Int. Cl.$^5$ .................... G01N 21/00; G01N 15/02; H01J 5/16
[52] U.S. Cl. .................................. 250/564; 250/574; 250/901; 250/227.25; 356/442; 356/336
[58] Field of Search .................. 250/573–576, 250/564–565, 227.21, 227.23, 227.25, 901; 356/441–442, 436, 338, 337, 336, 73

[56] References Cited

U.S. PATENT DOCUMENTS

| | | | |
|---|---|---|---|
| 3,872,315 | 3/1975 | Boll | 250/565 |
| 3,879,129 | 4/1975 | Inoue | 356/102 |
| 3,892,485 | 7/1975 | Merritt et al. | 356/103 |
| 4,040,743 | 8/1977 | Villaume et al. | 356/73 |
| 4,102,177 | 7/1978 | Okada et al. | 356/442 |
| 4,110,044 | 8/1978 | Pettersson et al. | 250/564 |
| 4,279,509 | 7/1981 | Daffern | 356/246 |
| 4,318,180 | 3/1982 | Lundquist et al. | 250/575 |
| 4,752,131 | 6/1988 | Eisenlauer et al. | 250/564 |
| 4,893,935 | 1/1990 | Mandel et al. | 356/442 |
| 4,940,902 | 7/1990 | Mechalas et al. | 250/573 |

FOREIGN PATENT DOCUMENTS

86/02162 4/1986 World Int. Prop. O. .

Primary Examiner—David C. Nelms
Assistant Examiner—Michael Messinger
Attorney, Agent, or Firm—Pollock, Vande Sande & Priddy

[57] ABSTRACT

An apparatus for preventing blocking of a measuring head intended for carrying out measurements on substances suspended in a flowing medium. A light beam is transmitted from a radiation source with a determined intensity which is essentially constant during the measuring process. the intensity of the radiation radiated from the medium is indicated with the aid of at least one radiation indicator. The electrical output signal of the radiation indicator is sent for evaluation to a signal processing device. An open measuring channel has two mutually opposing edges which are intended to be placed along the direction of medium flow. Radiation from the radiation source is emitted from the one edge and received at the other. Placed in connection with the measuring channel are radiation-conducting elements which are placed as close as possible to the outer part of the edges. All of the junctions between surfaces of different extension in the vicinity of the measuring channel are gently rounded.

26 Claims, 7 Drawing Sheets

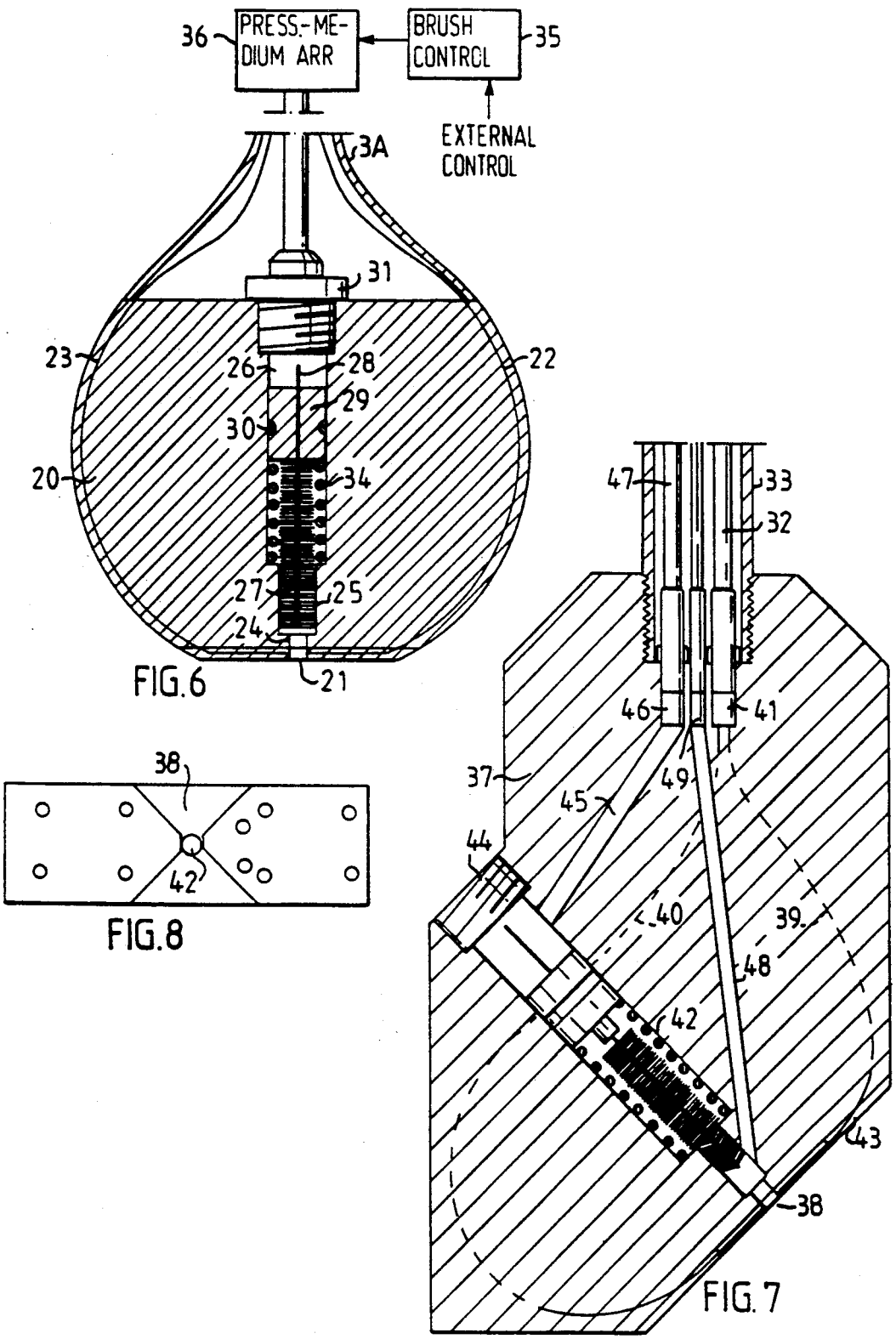

APPARATUS AND METHOD FOR PREVENTING BLOCKAGE OF A MEASURING HEAD FOR EFFECTING MEASUREMENTS OF SUSPENDED SUBSTANCES

FIELD OF THE INVENTION

The present invention relates to apparatus for preventing the blockage of a measuring head intended for effecting measurements on substances suspended in a flowing medium; and a method for registering the state of a moving suspension containing particle fractions of mutually very different sizes.

BACKGROUND OF THE INVENTION

The amounts in which material is suspended in different kinds of aqueous suspensions is an important measuring parameter, not least from the aspect of environmental care and protection. By suspended material is meant here generally such substances as those which can be separated mechanically by filtration and centrifugation. Especially in the forest industries, the suspended material may consist of many different components such as fibers, fiber fragments and various fillers and coating agents. These components may vary widely in size, from a few millimeters in length and some tens of microns in width (fibers) down to a particle diameter of about 1 micron and smaller (filler). The concentration of a suspension can vary within wide limits, from some mg/l to tens of g/l. It is important not only to measure the content of suspended material, but in many cases also to indicate when the size distribution of the suspended material changes, and the extent of this change. One area of use in this respect is to indicate the effect of the addition of flocculating chemicals.

The majority of instruments at present available on the market for continuously measuring suspended materials are based on optical measurement principles, e.g., on light absorption, light scattering and the influence of polarized light. The most common method comprises measuring the turbidity of the suspension, in which attenuation or scattering of light is used as a measurement of the suspended-material content. The extent to which light is scattered, however, depend not only on the concentration of the suspended material, but also on the particle size, shape, surface structure and refraction index of the material concerned.

Thus, suspensions in which the particle-size distribution varies considerably can give misleading information with regard to the concentration of the suspension. This is illustrated in FIG. 22, which discloses the result of turbidity measurements in which attenuation of the light transmitted through suspension was measured. The result (the output signal from the measuring apparatus) is shown as a function of the concentration of cellulose fibers (large particles) and for clay (small particles). As will be seen, such an instrument is far more sensitive to clay than to fibers for a given concentration.

U.S. Pat. No. 4,110,044 describes an optical method which, in principle, enables the concentration of suspended material to be determined independently of particle size. This measuring principle is based on recording not only the mean value of the light transmitted, but also on measuring fluctuations in light intensity, in the form of a signal which includes the square of the true effective value of an alternating voltage component of the measurement signal obtained. As a function of particle size, this value has a mirror-reversed behavior in relation to the signal which is based on the direct voltage component of the measurement signal. Consequently, the sum of these two signals will provide a measurement of the amount of material in the suspension independently of particle size.

Furthermore, it is possible to obtain a relative measurement of the particle-size distribution of the suspended material, by forming the quotient of these two signals.

This method is called the TP-method and is quite effective, particularly in the case of low concentrations, where good linearization of both the direct voltage signal and the square of the true effective value can be obtained.

However, in the case of suspensions having a particle-size distribution in which the particles are predominently large particles, the signal formed by the square of the effective value is influenced to a greater extent by the large particles than by the small particles. Another drawback, and one which is often serious in practice, is that the TP-method is relatively difficult to calibrate.

Another method which indicates the direct voltage component of the measuring signal and the effective value of the alternating voltage component of the measuring signal is described in U.S. Pat. No. 3,879,129. This has the same drawbacks as the TP-method.

In order for the TP-method, and similar methods based on measuring the effective value of the measuring signal to provide good accuracy with respect to particle content and good resolution with respect to particle size, it is necessary (depending on particle content and particle size) for the measured volume to be small and the light beam to be narrow. If essentially each particle is to produce a significant indication of the alternating voltage component of the signal, the illuminating light beam should be narrow and preferably collimated or focused, and the reflected light should be detected within a narrow angular range. The variations in alternating voltage are smoothed out when the light beam has a broad path. It is often desired to measure the suspended-material content of suspensions in which the proportion of suspended material is relatively high. In order to enable light radiated through the suspension to be indicated at all, the light source must be located comparatively close to the light detector. Consequently, it is usual to place the measuring apparatus in a narrowed or necked part of the measuring cell. This narrowed area of the measuring cell is prone to become blocked with large particles, suspended material-agglomerates and the like. Consequently, these narrowed measuring cell-areas are equipped with back-flushing devices and the like by means of which said area can be rinsed clean, when necessary.

One example of an arrangement of this kind is described in the article LASER OPTICAL METHOD FOR DYNAMIC FLOCCULATION TESTING IN FLOWING DISPERSIONS, by W. Ditter et al, BASF Aktiengesellschaft, from the book "The Effect of Polymers on Dispersion Properties", Academic Press, London 1982, pages 353–342. The suspension is led through a narrowed or necked measuring cell equipped with a measuring head arrangement. Light from a laser is focused onto the measuring cell and light exiting from the measuring cell is led to a photosensor. Another example of a similar arrangement having a short narrowed or necked part is described in U.S. Pat. No. 3,879,159 FIG. 2B. This arrangement also includes a known measuring head having an open channel which is intended to be immersed in a flowing suspension. This measuring head, which is based on fiber-optic techniques described in U.S. Pat. No. 3,879,159 has a very deep measuring gap or throat. Placed on the bottom of the gap is an optic which functions to emit light to the suspension flowing through the gap and to receive light exiting from the suspension. Because the gap is very deep, it will, in principle, function as a narrowed or necked measuring cell, and consequently will also give rise to the aforesaid blocking problem.

SUMMARY OF THE INVENTION

A concentration meter head shown in WO 86/02162 also has a very deep measuring gap. An optic is provided which gives a wide measuring beam through a paper pulp.

Still another measuring head is shown in U.S. Pat. No. 3,892,485. A measuring channel is shown, in which the whole suspension is flowing past an optical measuring arrangement. The upper part of the channel is turned inwardly with an edge in order to hold the flowing liquid on place inside the channel. This device is made for making measurements on oil, which is a quite pure liquid.

The main object of the present invention is to provide a measuring head operative to measure a flowing suspension with which the risk of blockages due to solid particles is minimized.

Another object of the present invention is to provide a measuring head in which the multiple scattering effect often caused by suspended particles in the suspension being measured is avoided to a large extent.

Still another object of the invention is to provide measuring apparatus which will illuminate the flowing suspension with a narrow light beam and detect the light transmitted or scattered by the suspension within a narrow angular range. The light beam may be collimated or focused.

Yet another object of the invention is to provide a particularly favorable method for evaluating the signal produced by the measuring head.

The width of the measuring beam is adapted so as to be the same size as or smaller than the interspaces between the larger particles in the suspension on which measurements are carried out. When measuring is effected with the intention of establishing the mutual distribution between the fine fraction and the coarse fraction of the suspended material, the width of the beam is adapted to the desired boundary line between the coarse and the fine fractions. The width of the measuring gap is adapted so that the multiple scattering effect of the particles present in the suspension will be as small as possible. Consequently, the width of the measuring gap will be small when the concentration of suspended material is high, and large when the concentration of suspended material is low. Naturally, the gap width will be larger than the size of the anticipated largest particles in the suspension on which measurements are carried out.

The constructional design of the measuring apparatus may vary widely, for instance with respect to the measurement indicator body intended for immersion in a channel or passageway or for embodiment in the walls of a tube intended for the throughflow of media, etc. The measuring apparatus may also be provided with several optical measuring channels, e.g., channels which operate with and without polarized light, light of mutually different wavelength, beams of mutually different diameters, etc. In this respect, it is possible to obtain appropriate information for respective measuring positions from the detector signal, with the aid of appropriate signal processing and correlation-measuring techniques. Measuring apparatus which have one or more optical measuring channels may also be provided with measuring detectors operative to measure scattered light, which can provide more information about the composition of the suspension. Simultaneous measurement of the transmitted and scattered light can also be employed to compensate for absorption effects in the suspension or in coatings on the optical surfaces, or to improve characterization of the composition of the suspension. A reference detector can be used to compensate for variations in intensity of the light source. Optical glass-fibers can be used with or without protection against the suspension being measured, depending on purpose and on measuring position. The ends of the fibers may also be provided with polarization filters, lens/index-lens, and protected with the aid of a quartz window, or sapphire window etc., without departing from the basic concept of the configuration of the measuring channel and measuring gap of the inventive measuring apparatus. When the measurement indicating body used is intended for immersion in flowing medium, the body will preferably be configured in a manner which will ensure that good flow conditions are achieved around the body, at least in the vicinity of the measuring gap or throat, so that the suspension will truly pass through the gap and so that the gap will be essentially self-cleaning. The region around the measuring gap is therefore provided with smooth surfaces and rounded edges.

BRIEF DESCRIPTION OF THE DRAWINGS

The invention will now be described in more detail with reference to the accompanying drawings, in which

FIG. 6 is a sectional view of a first embodiment of a measuring apparatus according to the invention with mechanical cleaning;

FIG. 7 is a sectional view of a second embodiment of a measuring apparatus with mechanical cleaning;

FIG. 8 is a top plan view of the side with the measuring channel in FIG. 7;

DESCRIPTIVE OF PREFERRED EMBODIMENTS

Figure 1:
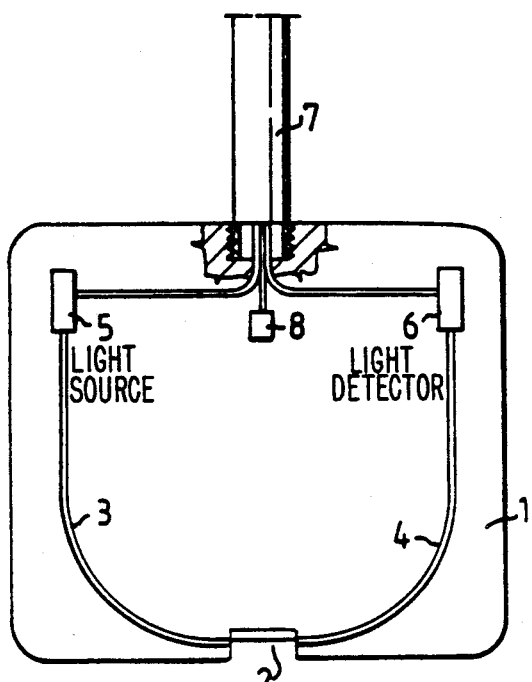
FIG. 1 is a front elevation of a first embodiment of an apparatus; according to the invention
Figure 2:
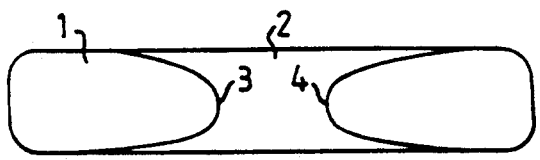
FIG. 2 is a bottom plan view of the apparatus illustrated in FIG. 1.

The measuring apparatus, or meter, illustrated in FIGS. 1 and 2 has a measurement indicating body in the form of a four-sided plate 1 with bevelled edges. The plate 1 forms a probe which is intended for immersion into a flow of suspension, with the broad side of the plate 1 facing towards the flow direction. The bottom surface of the plate has provided therein a groove 2 which functions as a measuring channel. The plate 1 has on one broad side thereof two rounded and comparatively deep grooves which connect at one end thereof with a respective side of the measuring channel and which extend parallel with the undersurface of the plate precisely at said connection. Each of the grooves has moulded therein a fiber-optic light guide 3, 4. The inner end of the guide 3 is connected to a light source 5, such as a photodiode or a small laser, which is also moulded in the plate. The inner end of the guide 4 is connected to a light detector 6 which is adapted to the light emitted by the light source and which is also molded in the plate 1. The electrical guides or cables leading to the light source 5 and extending from the light detector 6 are also molded in the plate and extend to and pass through a tube 7 screwed into the top of the plate. Because it is necessary to extend the fiber-optic light guides in a gentle arc, so as not to influence their performances, the channels carrying the guides 3 and 4 are given a gently curved configuration.

Both the light source 5 and the light detector 6 are temperature responsive components. Consequently, a temperature sensor 8 is molded in the plate 1 and an electric cable or fiber bunch extending from the sensor 8 is also passed through the tube 7 and connected to a signal processing circuit (not shown in the Figure) for the purpose of compensating for temperature when calculating the measuring result with the aid of the signal arriving from the light detector 6 in a manner described in more detail hereinafter. The surfaces of the plate 1 will preferably be smooth and also repellent, so as to avoid adherence thereon of material flowing past the plate, to the greatest possible extent. Naturally, the material from which the plate is made should be inert with respect to the medium in which the material is suspended, and also to the suspended material. The plate 1 is preferably made of a plastic or like material, although it may also be made of stainless steel.

The essential features of the invention reside in the configuration of the measuring channel together with the optics used. The width of the measuring gap between the side-walls is contingent on the type of medium on which measurements are to be carried out. For instance, if measurements are to be carried out on fiber suspensions in waste water that derive from the paper manufacturing industry, a width of about 3 mm may suffice. The edges of the gap will preferably be low and the fiber-optic light guides will be placed as close as possible to the outer edge of the gap, for manufacturing reasons. The underside of the plate, which holds the fiber-optic light guides in place, is preferably bevelled in the region of the measuring channel 2, whereas the end of the fiber-optic is preferably cutoff transversely to the direction of propagation and then severed end polished. The invention is primarily conceived for the detection of light transmitted directly through a suspension, and hence the fiber-optic light guides are placed with their respective ends opposite one another. However, as will become apparent from the description relative to FIG. 16, light which is scattered within a given angle can also be detected. As beforementioned, the optic, i.e. the ends of the fiber-optic light guides 3, 4 of the illustrated embodiment, shall be placed close to the outer edge of the measuring gap. As shown in FIG. 2, the channel inlet and outlet are also gently rounded in the flow direction, as is also the small part of the outer edge of the channel located externally of the optic. The fiber-optic will preferably have a given depth beneath the channel, such that the effect of friction between the flowing suspension and the bottom of the channel will have no appreciable influence on the suspension flowing past the fiber optic. The presence of sharp edges on the channel bottom should be avoided. All of these measures contribute towards providing a measuring head in which the risk of the channel becoming blocked is minimized. A closer description of the configuration of the channel is given later on with reference to FIGS. 7-10.

Figure 3:
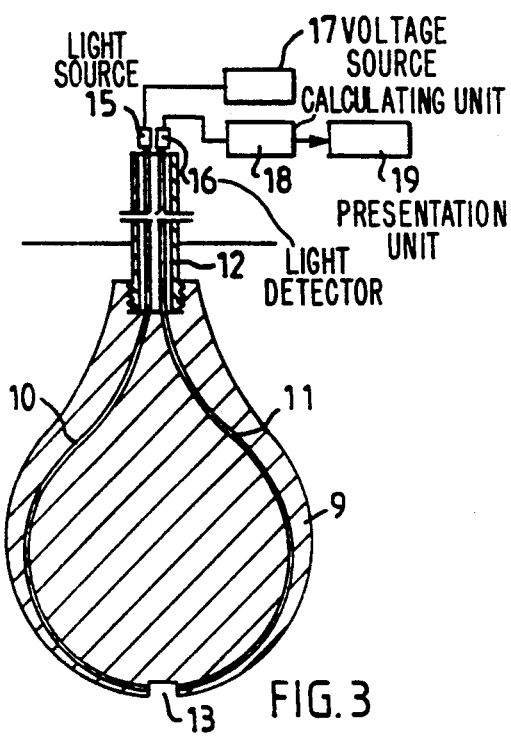
FIG. 3 is a longitudinal section view of a second embodiment of the apparatus, taken on the line III—III in FIG. 4.
Figure 4:
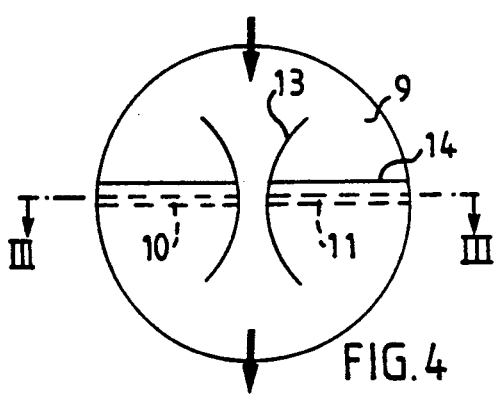
FIG. 4 is a bottom plan view of the embodiment illustrated in FIG. 3.

Preferably, the part of the measuring apparatus located in the medium or suspension, at least in the vicinity of the measuring channel, is given a somewhat streamlined configuration so as to reduce the risk of a change in form of the suspension passing through the measuring gap in relation to the actual or true composition of the suspension. In FIGS. 3 and 4, the measuring body has a rotational-symmetrical configuration. These Figures also illustrate an embodiment in which the fiber-optic light guides 10 and 11 are passed completely through the body 9 and through a tube 12 screwed into the upper end of the body 9, although it is conceivable, of course, to incorporate the light source, light detector and temperature sensor in the body. The body 9 is preferably pear-shaped, so that the fiber-optic light guides 10 and 11 can be extended in gentle curves from the measuring channel 13 up to and through the tube 12. FIG. 4 illustrates a suitable embodiment of the channel 13, having a broad inflow and outflow part and a narrowed or necked measuring gap part precisely in the region of the openings of the fiber-optic light guides 10 and 11 into the channel.

The body 9 is preferably manufactured in two parts, which are glued together along an interface 14. One of these parts, in FIG. 4 the bottom part, has cast or milled therein grooves for accommodating the fiber-optic light guides 10 and 11.

Figure 5:
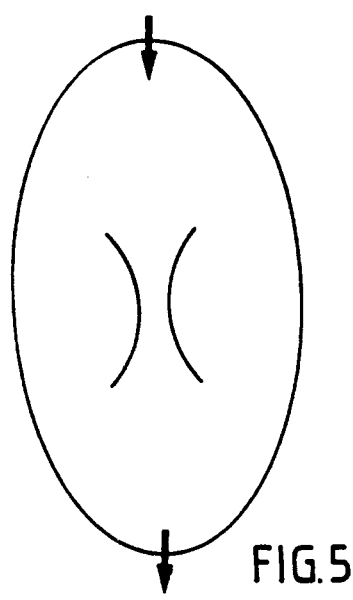
FIG. 5 is an alternative bottom plan view of the embodiment illustrated in FIG. 3.

The body 9 of the FIG. 5 embodiment has an elongated configuration in the flow direction. The section between the fiber-optic light guides is, in this case, the same as in FIG. 3. An even more streamlined configuration is conceivable.

In the FIG. 3 embodiment, a light source 15 for the light fiber-guide 10 and a light detector 16 for the light fiber-guide 11 are positioned in a part located on the end of the tube 12 externally of the suspension medium. If this location is stable with respect to temperature, there is no need to provide a temperature sensor for temperature compensating purposes. The light source 15 is supplied from a voltage source 17. The electrical output signal from the detector 16 is supplied to an evaluating and calculating unit 18. Appropriate calculations will be discussed hereinafter.

The calculation result is passed to a presentation unit 19, which may have the form of a display screen or a curve printer for continuous performance. The apparatus is intended primarily to provide quickly information concerning tendencies or trends towards changes in a suspension, so that monitoring personnel are able to notice immediately when something happens to change the suspension content of the monitored medium and to observe the effects of remedial measures taken.

The aforedescribed measuring units may be intended for immersion in a flowing suspension e.g., a suspension flowing in an open channel or passageway.

FIG. 6 illustrates a variant of the embodiment illustrated in FIG. 3, this variant incorporating mechanical cleaning of the head. The fiber light guides 22 and 23, shown solely in full lines, extended to the measuring channel 21, are located relatively close to the periphery of the measuring body 20.

The cleaning arrangement is placed in a central hollow or cavity in the body 20. The cavity has a first cylindrical part 24 whose diameter corresponds essentially to the measuring gap of the measuring channel 21, e.g., a width of about 3 mm, a second cylindrical part 25 of somewhat larger diameter, e.g., 5 mm, than the diameter of the first cylindrical part, and a third cylindrical part 26 of still larger diameter, e.g., 12 mm. A cylindrical brush 27 of essentially the same configuration as the dental brushes used to clean between the teeth has its stem 28 molded in a plunger 29 which moves in and which has essentially the same diameter as the third cylindrical part. The brush faces towards the outlet of the first cylindrical part 24. The second cylindrical part 25 functions as a brush guide, so as to prevent the brush from bending when moved outwardly through the opening at 24. The brush may also be caused to rotate during a cleaning operation.

A helical spring 34 is positioned between the plunger 24 and the shoulder formed at the junction between the second and third cylindrical parts 25 and 26. A ring-shaped seal 30 is fitted to the periphery of the plunger 29. The plunger can be operated either pneumatically or hydraulically, by supplying gas or liquid to the part of the plunger 24 distal from the measuring gap 21, through a closed channel 35 provided in the stem of the measuring body 20. A nipple 31 is screwed into the neck of the body 20, adjacent the third cylindrical part 26. Fitted onto the nipple is a hose which is connected to a pressure-medium arrangement 36 which, when brushing is to take place, supplies pressure-medium to the rear side of the plunger 29, so as to push the brush 27 out through the opening 24.

The stem 28 of the brush projects outwardly through a given distance from the plunger 24. When cleaning the brush 27 or replacing the brush together with the plunger, the nipple 31 and hose are removed. The end of the brush-stem is gripped with a suitable tool, e.g., snipe-nose pliers or the like, and the brush and piston are withdrawn through the cavity formed therewith.

The measuring process effected with the measuring head is carried out on a flowing suspension. Despite the particular configuration of the measuring gap with low, gently rounded edges, coatings will nevertheless form and consequently the measuring gap must be cleaned, preferably mechanically. The frequency at which the gap must be cleaned will depend on the composition of the suspension. A pressure-medium arrangement 36 operative to supply and remove pressure medium for operating the plunger 34 is controlled by a control circuit 35, which may be program controlled, time controlled, manually controlled or controlled by a combination of these types of control. The spring 34 is sufficiently strong to be able to move the brush back to a withdrawn position, even when part of the suspended material has adhered to the bristles of the brush. It may happen that particularly large suspended substances adhere to the bristles, so as to prevent the brush from being withdrawn completely into the measuring gap, or so that a fiber part projects from the gap. This will result in a marked indication in the measuring signal indicated by the evaluating and calculating unit (not shown in FIG. 6), and this unit will then supply a control signal to the control circuit 35, which subsequently causes the pressure-medium arrangement 36 to commence a new brushing cycle. If one or more additional brushing cycles fail to give the result desired, the evaluating and calculating unit can be constructed to deliver an alarm signal indicative of the fact that the brush must be cleaned or replaced.

FIGS. 7 and 8 illustrate the embodiment of a measuring body 37 at present preferred since this body can be manufactured and serviced in a simple fashion. The measuring body 37 of this embodiment is in the form of a flat plate whose periphery has an irregular configuration. The fiber-optic light guides 33 and 40 of the measuring body 37 are drawn to the measuring gap 38, these guides being shown schematically in full lines in those cases when the fibers lie on the same level as the illustrated section, and in broken lines when the fibers lie on a different level. The fiber guides are placed in gently rounded channels and are passed through a nipple 41 screwed into the body and supporting one end of a hose 32, from where the guides are extended to an evaluating and calculating circuit (not shown in FIG. 7). The hose extends in a tube 33 screwed to the top of the body 37.

In this case, the measuring gap is placed on a surface 43 which is oblique in relation to the surface along which supply lines are drawn to control and evaluating circuits. FIG. 8 is a view of the surface 43 containing the measuring-gap channel and the measuring gap 38 and the inlet of a channel 42 provided with a brush. The through channel 42 accommodating the brush arrangement has essentially the same configuration as the channel illustrated in FIG. 6, but is obliquely positioned in relation to the latter channel, since the channel of the FIG. 8 embodiment extends perpendicularly to the oblique surface 43. This provides a readily accessible opening on a side-part parallel to the surface 43, through which the brush arrangement can be serviced opposite the oblique surface. This opening is provided with internal screw threads and can be closed by means of a screwable lid or cover 44.

A pressure-medium channel 45, optionally in the form of a tube molded in the body, is provided between the channel 42 and a nipple 46 screwed into the body, the nipple having attached thereto a hose 47 which extends to a pressure-medium arrangement (not shown). The fiber-optic light guide 40 and the channel 42 are located at different levels in the body 37.

This embodiment includes a further channel 48 which extends between a nipple 49 screwed into the body and the channel 42, close to the measuring gap 38. A cleaning medium is supplied through the hose connected to the nipple 49, immediately prior to and optionally also during a brushing operation, for the purpose of improving removal of material adhering to the measuring gap. This will also enable the excessive adherance of suspended material to the brush to be avoided. The channel 48 can also be flushed clean between the individual brushing cycles. The cleaning medium may be either a gas, such as air, or a liquid, such as water, optionally admixed with chemicals.

Figure 9:
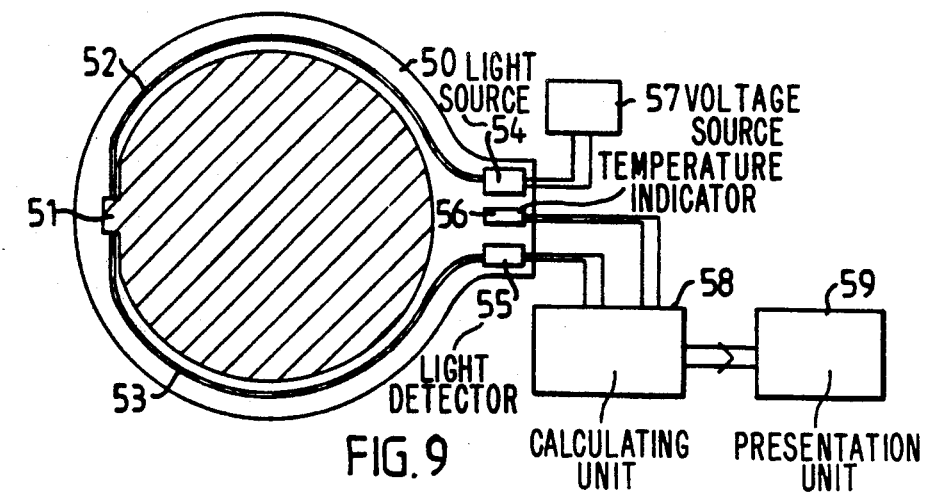
FIG. 9 illustrates still another embodiment of the measuring apparatus.

FIG. 9 illustrates a third embodiment of the inventive measuring apparatus which is intended to be inserted in a measuring cell or a tube through which a suspension flows. The measuring apparatus has the form of a tube 50 whose diameter is the same as the diameter of the measuring cell/tube in general. A measuring channel 51 is configured in a thickened part on the inside of the tube. The tube wall has placed therein two fiber-optic light guides 52 and 53 whose respective one ends are each connected to a respective side of the measuring channel 51, the other ends of the guides being connected respectively to units in the form of a light source 54 and a light detector 55. Since the units 54 and 55 are positioned so as to be influenced by the temperature of the medium being measured, a temperature indicator 56 is placed in the proximity of the units. A voltage source 57 is connected to the light source 54.

Similar to the aforedescribed embodiments, the signals from the units 55 and 56 are applied to an evaluating and calculating circuit 58, which is operative to calculate desired suspension data, e.g., concentration, particle-size distribution, fiber content, etc. The calculations are carried out continuously, with corrections being made for the temperature indicated by the indicator 56, and supplied to a presentation unit 59. The presentation unit 59 may, for instance, be a curve printer operative to print continuously curves representing one or more of the calculated properties of the suspension. Monitoring personnel can be made aware of trends occurring towards changes in the suspension by changes in the curve or curves, and may quickly observe the result of measures taken to change the composition of the suspension. These measures may involve the addition of flocculating chemicals to waste water with the intention of precipitating solid material. The tube 50 may include a plurality of measuring channels 51, for the purpose of measuring different properties of the suspension. These measuring channels may, for instance, be disposed sequentially in the flow direction, or located at mutually different positions around the tube circumference (not shown). For instance, the particle-size distribution of a suspension may be measured with the aid of two or more measuring channels with mutually different diameters of the transmitted beam path. An example of this kind of signal processing technique is described in SE 7806952.

Figure 10:
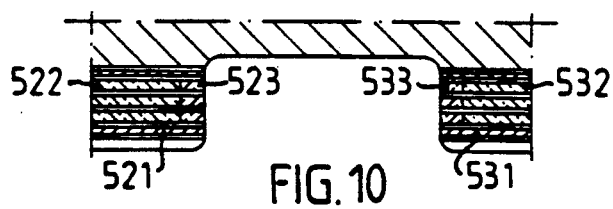
FIGS. 10-14 are longitudinal section views in larger scale of alternative configurations of the region nearest the measuring channel of the measuring apparatus appropriate for all the illustrated embodiments of the apparatus.

Instead of using a plurality of measuring channels of mutually different diameters, cables comprising multiple optical fiber guides (fiber bundles) can be disposed in the manner of the cables 52 and 53 (or as 3, 4 in FIGS. 1 and 10, 11 in FIG. 3), and a different number of fiber guides are illuminated and light therefrom detected respectively in order to determine particle-size distribution. One embodiment of a measuring gap having these properties is illustrated in FIG. 10. A transmitter cable 521 includes N number of fiber-optic light guides 525. In order to collimate or focus the emitted beam, each fiber-optic light guide 522 is provided with an index-lens 523 at the end thereof adjacent the channel. Similarly, a receiver cable 531 includes N number of fiber-optic light guides 532 which are disposed immediately opposite each of the fiber-optic light guides 522. Each fiber-optic light guide 531 is also provided with an index-lens 533 adjacent the measuring channel. The fiber-optic light guides 522 can either be illuminated by a common light source or by an individual light source (not shown). The ends of the fiber-optic light guides 532 remote from the measuring channel are each connected to a respective light detector or to a mutually common light detector (not shown). For the purpose of indicating particle-size distribution, the signals from mutually different numbers of light detectors can be added together and a comparison made between the different signals obtained in this way. FIGS. 11–14 illustrate different embodiments of the region adjacent the measuring gap in the aforedescribed embodiments of the measuring apparatus.

Figure 11:
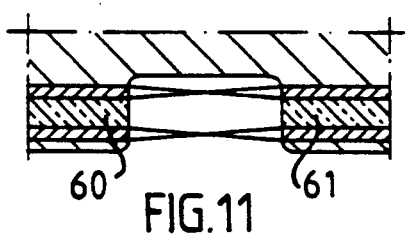
Figure 12:
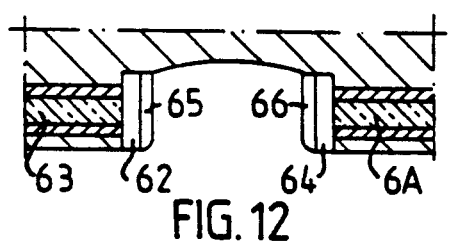

In FIG. 11 the ends of the fiber optic-light guides are connected directly to the measuring channel and are placed centrally opposite one another. Each fiber optic light guide includes, in a conventional manner, a core with one or more casings having a refractive index different from the core, and also a protective sheath. The ends of the light fibers guides 60 and 61 are ground flat. The light exiting from a light-emitting fiber-optic light guide is slightly divergent, and a light-receiving fiber-optic light guide has a slightly divergent field of view. If, for instance, a fiber-optic light guide having an outer diameter of 1.0 mm and a core diameter of 0.6 mm is used, the emitting and the receiving light cone respectively can be considered to be narrow when the length of the measuring gap is between 1 and 5 mm. A measuring-gap length of 3 mm is appropriate in the case of many applications.

When measuring optically-active suspended material, e.g., fiber material, polarized light is emitted from the measuring apparatus, and light of rotated polarization is received from the suspension. In this case, a polarizer 62 can be positioned at the end of the emitting fiber-optic light guide 63, as shown in FIG. 9, and a polarizer 64 which is phase shifted through 90° relative to the polarizer may be positioned in front of the end of the receiving fiber-optic light guide 65. Each of the polarizers 63 and 64 may be protected by a respective sapphire-glass plate 65 and 66 positioned between the measuring gap and the polarizers. As will be seen from FIG. 12, the bottom of the measuring channel need not necessarily be flat, but may be gently rounded in its entirety.

Figure 13:
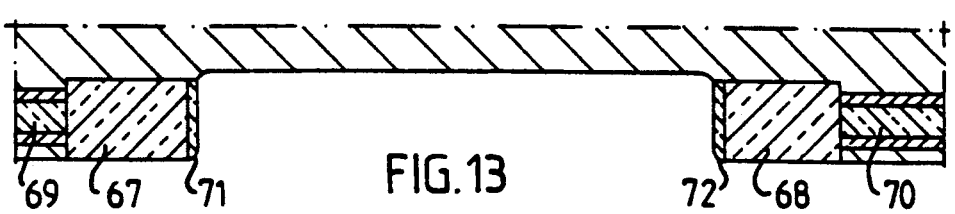
Figure 14:
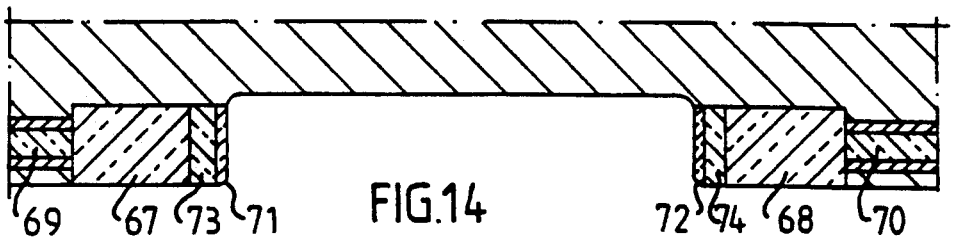

If measurements are to be made on a thinned or diluted suspension, the measuring gap may well be relatively long in order to achieve good accuracy. Examples of such cases are illustrated in FIGS. 13 and 14. In this case, a lens 67, 68, e.g., of the index-lens type, is positioned between each of the fiber-optic light guides 69 and 70 and the measuring gap, so as to collimate or possibly focus the beam and thereby obtain a narrow beam. The lenses 67 and 68 are protected against the corrosive and mechanical influence of the suspension being measured, by means of a hard sapphire plate 71 and 72, respectively. FIG. 14 illustrates an embodiment in which polarizers 73 and 74 are each positioned in the beam path, either between the lens and the sapphire plate, as in the FIG. 14 embodiment, or between the lens and the fiber-optic light guide (not shown). Consequently, the width of the measuring gap is preferably adapted to the anticipated concentration of the suspension to be measured by the measuring apparatus. High concentrations give a small width, low concentrations give a large width.

It should be observed that all of the optical components used have a small dimension transversely to the optical axis, so as to obtain a low measuring-gap height. Furthermore, the junction between the bottom of the measuring channel and the side edges should be rounded as far as is possible in practice, as illustrated in FIG. 11. All surfaces should be smooth.

Figure 15:
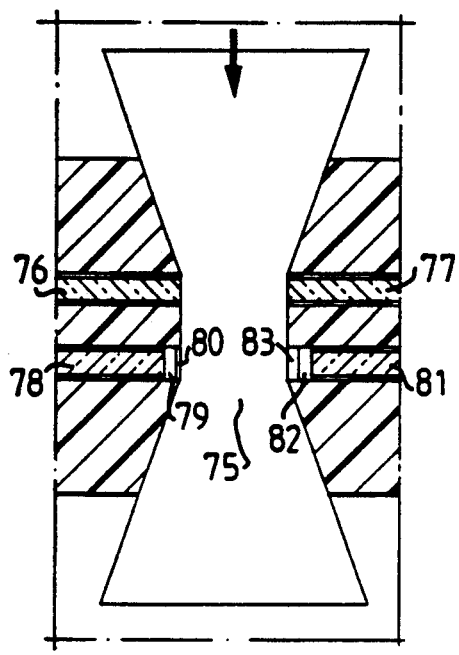
FIGS. 15 and 16 are sectional views of the measuring apparatus for two different alternatives of an arrangement for multiple beam indication.

As will be understood, more than one measuring beam can be transmitted through the suspension. FIG. 15 illustrates an embodiment in which two measuring paths are located adjacent one another in the measuring channel 75. In the case of this embodiment, these paths have the same measuring-gap width, although different measuring-gap widths are also conceivable. Light transmitted directly through the measuring channel from a fiber-optic light guide 76 is received by a fiber-optic light guide 77. A fibre-optic light guide 78 positioned adjacent the fiber-optic light guide 76 is terminated by a polarization filter 79 and a protective quartz or sapphire window 80 at locations adjacent the measuring channel. A fiber-optic light guide 81 disposed adjacent the fibre-optic light guide 77 is terminated by a polarization filter 82 and a protective quartz or sapphire window 83 adjacent the measuring channel. This enables two properties of the suspension to be measured simultaneously, for instance the particle concentration and some other property of the particle composition which produces an optical rotation in polarization.

Figure 16:
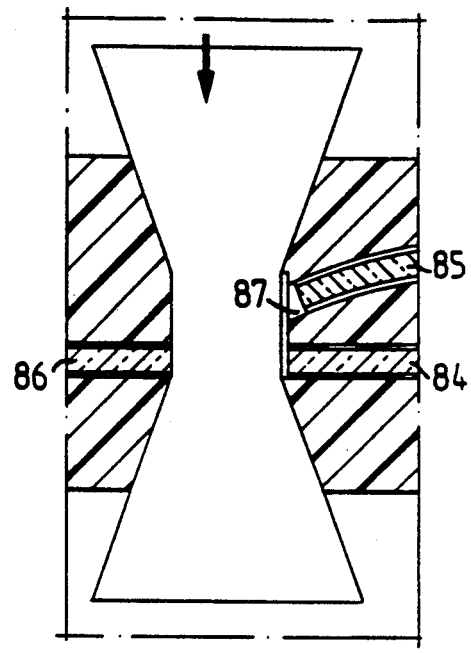

FIG. 16 illustrates an embodiment in which two fiber-optic light guides 84 and 85 are positioned to capture light emitted from the same fiber-optic light guide 86. The fiber-optic light guide 84 catches light transmitted through the suspension and the fiber-optic light guide 85 catches light deflected through a given angle by the suspension. A quartz window or sapphire window 87 provides a smooth surface along the light catching side of the measuring channel. The sapphire window 87 is not necessary, however. In some applications, where scattered light is to be indicated, solely the fiber-optic light guide 85 is necessary, and the fiber-optic light guide 84 can be omitted.

It is obvious that combinations of multiple measuring paths other than those illustrated in FIGS. 15 and 16 are possible. For instance, different measuring paths for light or different wavelengths can be used. Particle-size distribution can be determined, for instance, by varying the sensitivity of the particle-size measuring process in accordance with fiber diameter.

Figure 17:
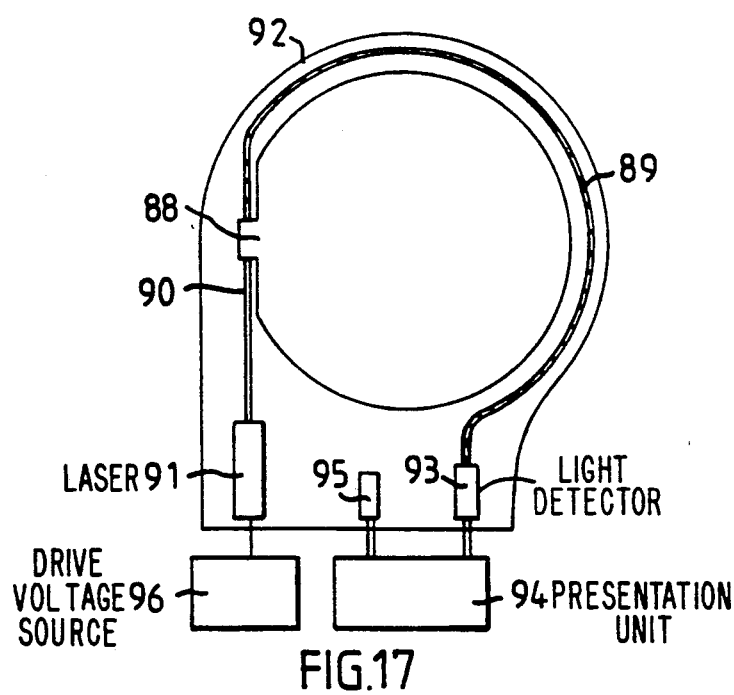
FIG. 17 illustrates a fourth embodiment of the invention.

FIG. 17 illustrates a further embodiment of the measuring apparatus. This apparatus is a variant of the apparatus intended for measuring cell/tube throughflow illustrated in FIG. 9, although the principle can also be applied to variants of the other aforedescribed measuring apparatus. Instead of a fiber light-guide for the emitted light beam, the FIG. 17 embodiment has a straight channel 90 extending to the measuring channel 88 in the thickened part of the measuring cell/tube 89. A laser which sends a narrow light beam through the channel 90 is placed at the other end of the channel. Located on the opposite side of the measuring channel 88 is a fiber light guide 92 which passes around the tube 89 and leads to a light detector 93, the electrical output signal of which is applied to a calculating and presentation unit 94, as is also the output signal from a temperature sensor 92. A drive-voltage source 96 is connected to the laser 91.

It is stated in U.S. Pat. No. 4,110,044, referred to in the introduction, that the suspended-material content of the suspension can be determined with the aid of the square of the effective value on the alternating voltage component of the signal from the light detector. When using the measuring apparatus provided with a short measuring gap, it is possible to indicate the content of suspended material at much higher concentrations than was previously possible by transmitting light through the suspension. When using a narrow beam in relation to the interspaces between large particles in the suspension, the alternating voltage component of the detector signal is able to give an indication of the suspended material that flows past, with good resolution.

A novel signal-processing method has been found very suitable for use with the measuring head, of the invention since that head is able to provide the well-demarcated and narrow beam path and a measuring gap of small width required for the signal-processing method when measuring suspensions typical of the pulp and paper manufacturing industry, for instance. The novel method is based on a first assumption that the suspension will in principle consist of two components, large and small particles. The large particles can then be considered as a relatively transparent network in which many small particles are suspended. When a minor part-volume of such a suspension is considered in accordance with statistic distribution principles, the number of small particles will be large and relatively constant. The number of large particles, on the other hand, is very small and varies greatly.

A suspension of fibers 1 mm in length and 20 microns in width and having a concentration of 1000 mg/l will, for instance, contain approximately two particles per mm$^3$. If 100 mg/l clay having a particle size of 1 micron in diameter is added to this suspension, the number of particles will increase to $7.5*10^4$ per mm$^3$. When measuring light attenuation in a minor volume of this suspension, a mean value of the intensity of the transmitted light will be obtained. Deviations from this mean value are caused primarily by fluctuations in the fiber material (the fibers enter the light beam from time to time). In principle, the greatest signal height is obtained when no fibers are present in the light beam and the light beam is attenuated solely by the clay particles. This enables the proportion of large or small particles in the suspension to be determined by measuring the mean value $V_{DC}$ of the light transmitted and the maximum value of said light, i.e., peak values $V_p$, over a predetermined time period. (In this connection, light-absorbing, dissolved substances in the suspension function in the same manner as clay and can be determined by measuring the peak value $V_P$.

Lambert Beer's law is used to calculate the turbidity or concentration of the suspension, this law giving the intensity of transmitted light in accordance with the following relationship:

$$V = Vo * e^{-alN} \qquad (1)$$

where

Vo = the intensity of the light transmitted for clear water, i.e., water having no particles suspended therein.

V = the mean value of the light intensity attenuated by the presence of particles. a = the scattering coefficient.

l = the length of the light beam-path through the suspension.

N = the number of particles per unit of volume.

The turbidity is normally defined as $$= N \cdot a = \ln(VO/V)/l \qquad (2)$$

It will be seen from the aforegoing that the turbidity is directly proportional to the concentration of the suspension for one and the same type of particle.

The following relationship applies in the case of suspensions which comprise a plurality of different types of particle:

$$= \Sigma N_i \cdot a_i = (1/l) \cdot \Sigma \ln(V_O/V_i) \qquad (3)$$

where i is an index for different types of suspensions, the summation being made over all particle types. The concentration of the suspension in mg/l is hence:

$$\text{conc} = (1/l) \cdot \Sigma C_i \cdot \ln(V_O/V_i) \qquad (4)$$

where $C_i$ are constants for converting the turbidity to concentration in mg/l for respective particle types.

If the suspension concerned consists of a mixture of two completely different types of suspensions, i.e., a suspension having very small particles, e.g. clay, and a suspension having relatively large particles, e.g. fibers, these particles will have a mutually different effect on the light transmitted, as mentioned above. Generally speaking, it can be said that the suspension part containing the small particles will have an affect on the deviation of the maximum signal height from the signal obtained when measuring clear water, whereas the suspension-part containing the large particles will result in a clear variation (changing) of the signal.

Figure 18:
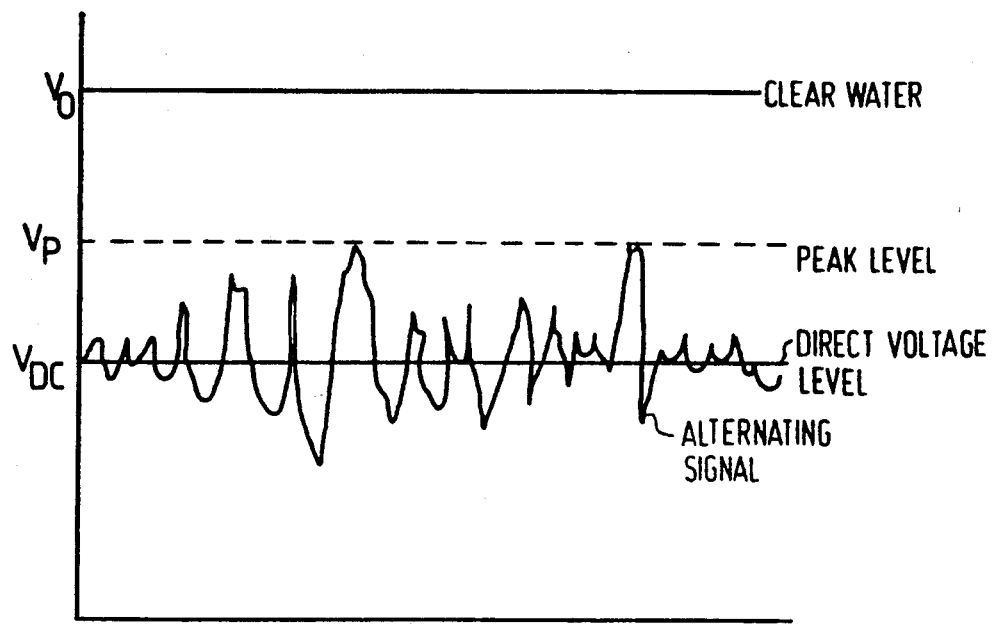
FIG. 18 is a diagram which illustrates the output signal from the detector of the measuring apparatus and showing a number of parameters.

FIG. 18 is a diagram which illustrates the alternating voltage signal obtained from the inventive measuring head. The levels of the clear-water signal $V_O$ (these levels having been measured earlier when calibrating the instrument by measuring on clear water), the direct voltage level $V_{DC}$ of the signal and the peak level $V_P$ of the signal are shown. Since, in accordance with the aforedescribed theory, the small particles will have no appreciable influence on the variation of the resultant signal, but primarily cause the peak value of the signal to be lowered from the clear-water level to the peak value $V_P$ there is formed for this part of the suspension $\ln(V_O/V_P)$, whereas $\ln(V_P/V_{DC})$ is formed for the suspension-part containing the large particles.

Thus, the application of Lambert Beer's law for a "model suspension" consisting of two particle types—large and small—will give the following result for the signals in FIG. 17:

$$\text{conc.} = a \cdot \ln(V_O/V_P) + b \cdot \ln(V_P/V_{DC}) \qquad (5)$$

where a and b are constants, $a \cdot \ln(V_O/V_P)$ is the concentration of small particles and $b \cdot \ln(V_P/V_{DC})$ is the concentration of large particles.

The above equation (5) can be rewritten as follows:

$$\text{conc} = (\ln(V_O/V_P) + c_1 \cdot \ln(V_P/V_{DC})) \cdot c_2 \qquad (6)$$

where $c_1$ is the sensitivity coefficient of the measuring apparatus and $c_2$ is a constant for converting the measurement values to concentration in mg/l. It is found that these constants can be readily obtained, by calibrating the measuring apparatus.

Figure 20:
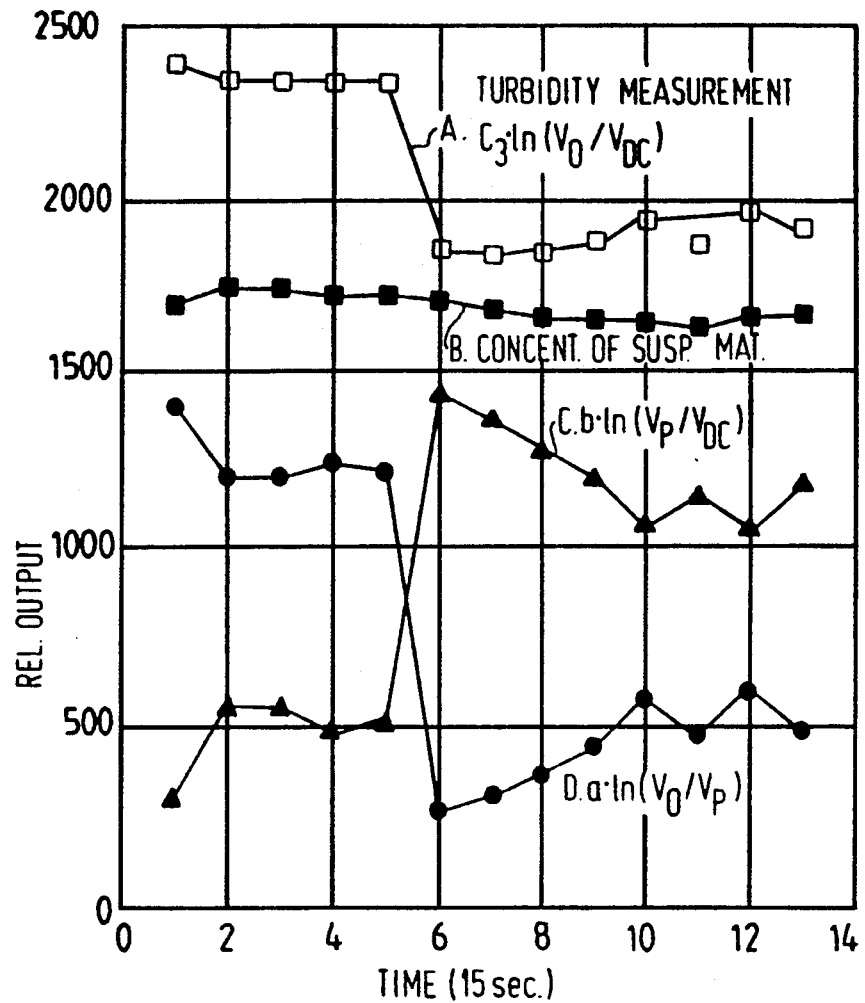
FIG. 20 is a diagram of a curve scale obtained when testing the invention.
Figure 22:
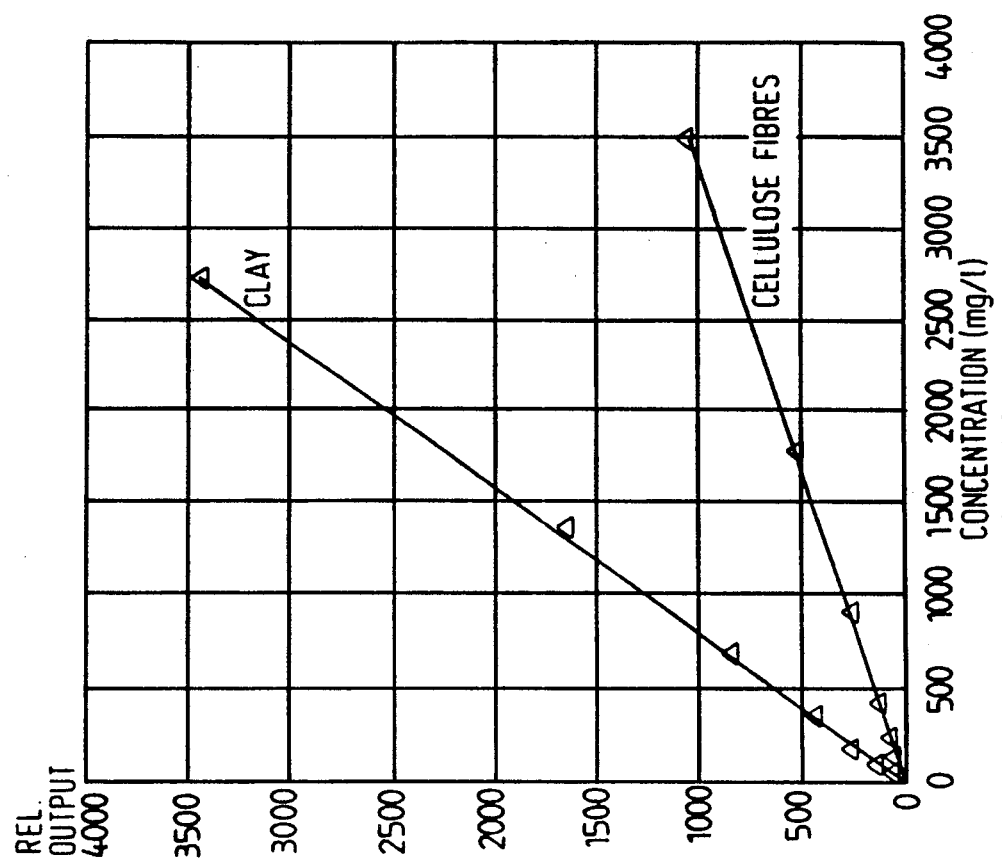
FIG. 22 illustrates the result of measuring the concentration of suspended material of different particle sizes carried out with a known concentration meter.

These constants were readily obtained experimentally, by measuring two suspensions having the same concentration, containing on one hand the smallest particles and on the other hand the largest particles;

$$(\ln(V_O/V_P))_s + c_1 \cdot (\ln(V_P/V_{DC}))_s = \ln(V_O/V_P)_l + c_1 \cdot (\ln(V_P/V_{DC}))_l.$$

where s signifies small particles and l signifies large particles $$c_1 = \frac{(\ln(V_O/V_P))_s - (\ln(V_O/V_P))_l}{(\ln(V_P/V_{DC}))_l - (\ln(V_P/V_{DC}))_s}$$

$$c_2 = \frac{\text{conc. lab}}{\ln(V_O/V_P + c_1 \cdot \ln(V_P/V_{DC}))}$$

where conc.lab is a value of the suspension concentration obtained when determining measurements in the laboratory in accordance with standard methods. Several such measuring processes may be carried out, of course, preferably with different concentrations, so as to obtain a result which is more positive statistically.

ln $(V_O/V_P)$ and ln $(V_P/V_{DC})$ can be used together with the calculated conc-value for the purpose of calculating the percentual composition of the suspension with respect to small and large particles respectively, as will be described in more detail hereinafter with reference to FIG. 20. The quotient of ln $(V_P/V_{DC})$ and ln $(V_O/V_P)$ will provide another relative measurement of particle-size distribution.

Figure 19:
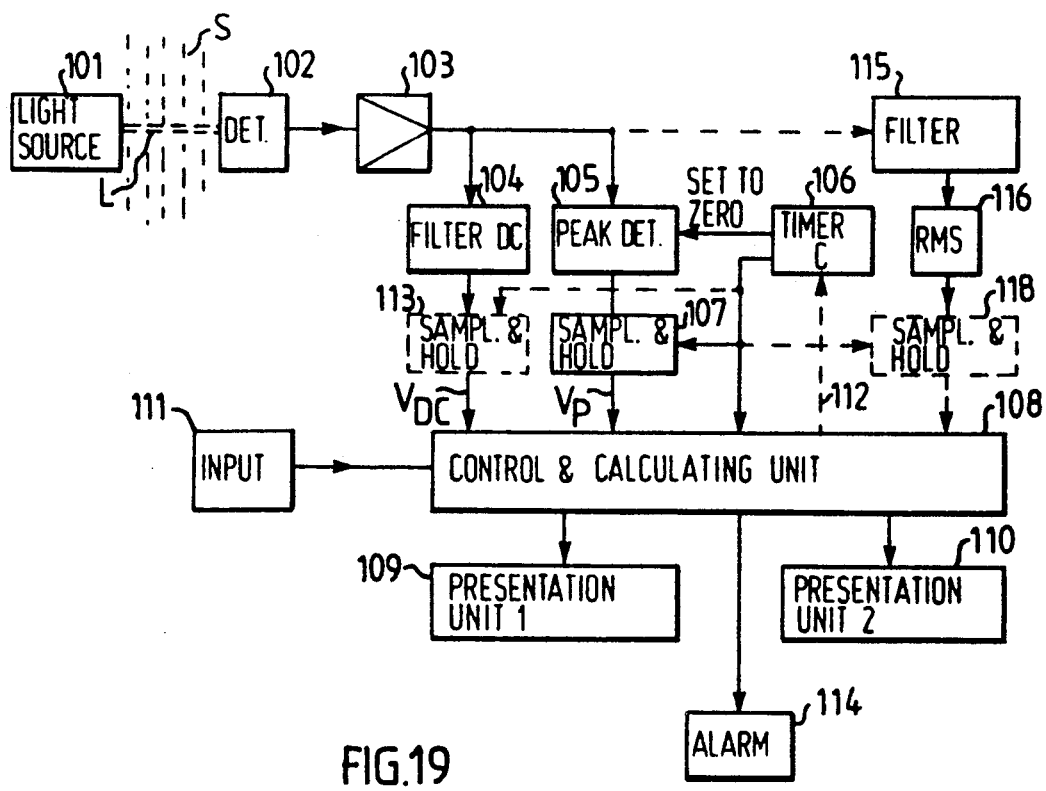
FIG. 19 is a block schematic of one embodiment of signal processing apparatus.

FIG. 19 illustrates an embodiment of apparatus for carrying out the inventive method. A light beam L from a light source 101 illuminates a flowing suspension S. The diameter of the light beam L is small in relation to the interspaces between the large particles in the suspension, but large in relation to the interspaces between the small particles. In practice, this will often lead to an endeavor to obtain a narrow light bundle.

The transmitted light is detected by a photosensor 102. The sensor signal is amplified in an amplifier 103. Connected to the output of the amplifier 103 is a filter or mean-value former 104, which produces on its output the direct current component $V_{DC}$ of the signal, this component providing a measurement of the mean value of the transmitted light. Connected to the amplifier output is also a peak detector 105, which registers the largest signal $V_P$ for a given measuring period.

The measuring period is set with the aid of a timer 106. At the end of each measuring period, the timer 106 sends a first signal to a sample and hold circuit 107, the input of which is connected to the output of the peak detector 105, so as to store temporarily the prevailing output signal from the peak detector 105, and after a slight delay sends a second signal to the peak detector 105 for the purpose of setting said detector to zero in readiness for a new measuring period. Consequently, the peak values $V_P$ for the immediately preceding period will always be present on the output of the sample and hold circuit 107. It is also possible to control the light source 101 in a pulsating manner, and to carry out measurements solely during the pulses. This control (not shown) is effected by the unit 108, which controls the circuits 105 and 107 in accordance therewith.

The signals $V_{DC}$ and $V_P$ are supplied to a control and calculating unit 108, suitably a microprocessor, for instance an IBM-compatible PC, which carries out the aforedescribed calculations and presents the results on at least one presentation unit 109, 110, e.g., a monitor, printer and the like.

The measuring period of the timer 106 is adapted so that in all probability a peak value will occur within each measuring period, but is nevertheless kept so short that changes in the suspension will be indicated as soon as possible after they occur, and so that variations of the changes in time can be followed continuously. This enables the measuring periods to be kept short when the coarse-fraction concentration is low, although these periods should be longer with increasing concentrations of the coarse fraction. The duration of the measuring period can be made variable in accordance with predetermined parameters, which may optionally depend on measuring results earlier obtained.

It may also be suitable to control a sample and hold circuit 113 with the aid of the timer 106 in the same manner as the sample and hold 107 downstream of the filter 104. The sample and hold circuits 107 and 113 are of the kind operative to transmit their values in digital form to the digitally operating unit 108. It will be obvious to the person skilled in this art that a part of the circuits 104-107 and 113, or all of these circuits, can be simulated by software in the unit 108, although the signal or signals supplied to the unit 108 will, of course, be converted to the signal format with which the unit 108 operates. Such conversion units have no significance in the present context and are therefore not shown. For instance, the filter 104 may consist of a calculating or aritmethical routine which calculates the mean value of the signal during each measuring period. The signal from the amplifier 103 may be sampled by the units 104 and 105 and all calculations effected digitally in a manner well known to those skilled in the art.

As also illustrated in FIG. 19, calculations can also be effected in accordance with the abovementioned TP-method or may be based on solely effective-value measurements. It may be advantageous to calculate mutually the same properties of the suspension in accordance with two different methods and to continuosly compare the results and send an alarm signal to an alarm unit 114, e.g., an audio alarm or an optical alarm, as soon as the calculations made in accordance with the two methods deviate from one another in a predetermined manner.

Comparisons with methods based on effective-value measurements do not involve significant additional measures, since it is possible to utilize the same fundamental signal from the measuring head 101, 102, 103. Consequently, a filter 115 is shown connected to the output of the amplifier 103. The filter 115 is operative to filter out the alternating voltage component of the signal and to supply this component to a unit 116 operative to measure the true effective value of the signal arriving from the filter 115 and to supply this value to the unit 108, optionally via a sample and hold circuit 118 of the same type and operational function as the circuits 107 and 113. The signal paths are shown in broken lines, to indicate that the elements 115, 116 and 118 can be excluded. It will be understood that the elements 115, 116 and 118 can also be simulated by program loops in the unit 108.

FIG. 19 illustrates only one measuring head 101, 102. In this case, a division is made into solely two particle-size ranges, large and small. An indication in several size classes can be obtained, however, by using several measuring heads having beam paths of different widths. Measuring equipment having these properties for the TP-method is described in SE 7806922. The described signal processing method according to the invention can be applied on the signals from all of the heads. In this case, the control and calculating unit 109 obtains a $V_{DC}$-signal and $V_p$-signal from each measuring head and is provided with a program which calculates the particle concentration within a number of particle-size ranges.

For the purpose of testing the inventive method experimentally on particle sizes, experiments were carried out initially on suspensions which contained very small particles. Different flocculating chemicals were then added to these suspensions while agitating or stirring the suspensions continuously, such as to form large particle agglomerations or flocs. The results of these measuring operations are given in FIG. 20. The curve A illustrates turbidity measurement which corresponds to $C_3 * \ln(V_O/V_{DC})$, where $C_3$ is a constant.

The curve B shows the results obtained when measuring the concentration of suspended material in accordance with the invention, i.e., conc=$c_2*(\ln(V_O/V_p)+c_1*\ln(V_p/V_{DC}))$. The curve C represents $b*\ln(V_p/V_{DC})$, i.e., the concentration of large particles in the suspension. It is found that, in principle, $\ln V_p/V_{DC}$ is independent of variations in light intensity and also dirtying and scratches of the optical surfaces. The curve D represents $a.\ln(V_O/V_p)$, i.e., the concentration of small particles in the suspension. The curves have been marked with different types of signs. Each sign, or marking, is placed on a measuring time-point, which is marked along the abscissa. There is a time period of 15 seconds between each measuring time-point.

The measurements were carried out in the laboratory on white water obtained from a paper machine. The water was untreated at measuring time-point 1. Different flocculating chemicals were added to the water on two occasions, immediately prior to measuring time-points 2 and 6. As will be seen from curves C and D, the first chemical, added at measuring time-point 2, had a relatively small flocculating effect, whereas the second chemical, added at measuring-point 6, had a relatively large effect. This is also shown by the curve A obtained in accordance with the earlier known turbidity method, although not as clearly. The curve C is practically a mirror-image of the curve D. These curves show that the flocs are degraded slowly subsequent to the heavy formation of flocs at the measuring time-point 6, i.e., the curve D falls and the curve C rises. A certain tendency in this direction is also observed after measuring time-point 2. Curve B, which is a weighted addition of the curves C and D, lies practically on the same level, which can be taken as an extraordinarily good result, since this curve would show the total concentration, which has been held constant during the laboratory measuring process.

The curves obtained when practising the inventive method indicate that clear information can be obtained continuously with regard to the state of, e.g., a flowing suspension, and that an indication of the result of measures taken when adding different chemicals can be obtained rapidly and positively. As shown by curve D, it can be seen when the chemical addition is such that the addition of further chemicals will not have a greater effect with regard to the flocculation of small particles. When chemicals were added at time-point 6, the curve D fell so low as to lie relatively close to the x-axis. The operator can endeavor to lower the curve still further, by adding more flocculating chemicals. If the curve fails to fall to a lower level, the addition of further chemicals will have had no effect on the flocculation of residual small particles, this circumstance being indicated immediately. Other agents can then be tested, the effect of these agents also being shown on the curve immediately after their addition. Thus, the inventive method will enable the metering of chemical flocculating agents, e.g., into white water obtained from a paper mill and when pulp cleaning to be controlled optimal fashion. Furthermore, the effect produced by different chemicals can be quickly seen, thereby enabling the chemical best suited for the purpose to be used.

Figure 21:
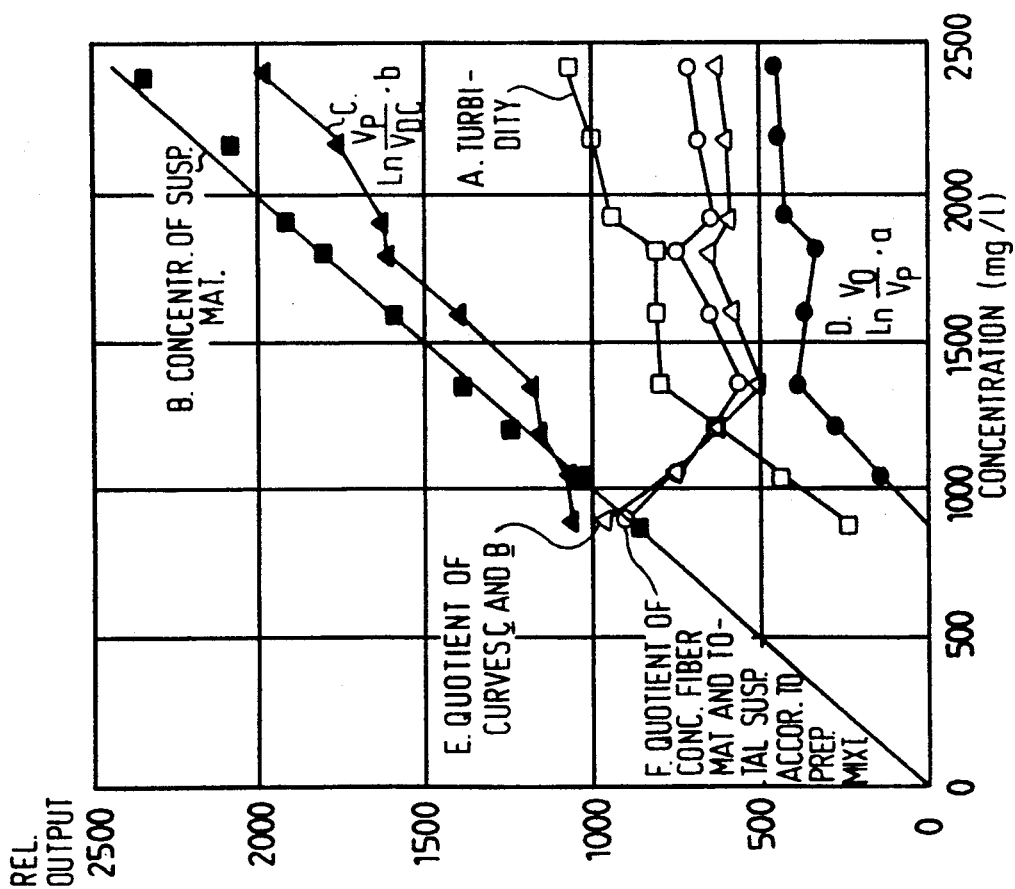
FIG. 21 is a diagram comprising a number of curves obtained when carrying out experiments with the invention with successively increasing concentrations of suspended materials.

FIG. 21 illustrates the results obtained when practicing the inventive method with various mixtures of fiber and clay suspensions of known concentration. Similarly to FIG. 20, the curve A shows the results of turbidity measurements, the curve B shows the results obtained when measuring the concentration of suspended material in accordance with the invention, i.e. $C_2*(\ln (V_O/V_P)+C_1*\ln (V_P/V_{DC}))$, the curve C $b*\ln (V_P/V_{DC})$ and the curve D $a*\ln/V_O/V_P)$. The curves E and F illustrate respectively the measured and calculated concentrations of large particles in relation to the total concentration. There were added successively to a starting suspension of pine sulphate pulp known contents of clay, clay, clay, pine sulphate, pine sulphate, clay, birch sulphate, birch sulphate. When applying the inventive method, the measured concentration, which was found to increase almost linearly, correlated very well with the concentration determined in the laboratory (abscissa). The measured content of large particles (curve E) also coincided very well with the calculated proportion of fiber material according to the mixing procedure (curve F). As will be evident from curve A, in the case of the variations in composition of the suspensions used here, these variations being realistic within the forest industries, turbidity would definitely be the wrong measuring parameter to use when wishing to obtain knowledge of the events taking place with the suspension, both with respect to the content of suspended material and to the particle size distribution.

The inventive principle can also be applied when measuring in accordance with the scattering principle. This can apply, for instance, when the suspension contains very low proportions of suspended material. In the case of this measuring procedure, a small signal is measured relative to the background at the O-level instead of a small signal change relative to a high background level (the clear-water level) as in the case of transmission measuring processes. This can involve indicating the bottomn value $V_B$ of the alternating voltage signal instead of indicating the peak value in FIG. 18, and placing this bottom value in relation to the zero level instead of to the clear-water level for the suspension-part containing the small particles. For the suspension-part containing the large particles, the bottom value $V_B$ is placed in relation to the mean value level $V_{DC}$. These relationships, however, are more complicated than the simple logarithmic quotient expressions for transmission measurements and, inter alia, are contingent on the geometric configuration of the measuring apparatus.

When measuring typical suspensions, such as white water or backwater deriving from a paper mill, the inventive measuring method requires a relatively narrow measuring beam which is substantially collimated or focused. The suspensions are often relatively concentrated, which requires a small measuring gap in order to enable light transmitted through the suspension to be indicated and in order to provide a processable, received signal. Known measuring heads possessing these properties are liable to become blocked and must be cleaned often.

It will be understood that many modifications are possible within the scope of the invention. For instance, the measuring channels can be constructed for use with radiation other than light radiation, e.g., for $\beta$-radiation.

The embodiments illustrated in FIGS. 9 and 17 may also be provided with an arrangement for cleaning the measuring gap of essentially the same kind as those illustrated in FIGS. 6 and 7.

I claim:

1. Apparatus for preventing blockage of a measuring head for effecting measurements regarding concentration of substances suspended in a flowing medium, said measuring head comprising:
   (a) an open measuring channel which has two mutually opposing channel sides;
   (b) at least one measuring beam transmitted from one side of said channel from a beam source of substantially constant and predetermined intensity during a measuring process;
   (c) radiation indication means for indicating an intensity of the beam transmitted through said medium and received at the other side of said channel, and in which an electric output signal of said radiation indication means is supplied for evaluation to a signal processing device;
   (d) a thin transmitting light channel, such as a fiber-optic light guide or a narrow straight channel having a size substantially of the order of said fiber-optic light guide, which transfers a narrow beam, for transmitting said measuring beam from said beam source to said other channel side to said radiation indicator;
   (e) said light channels, adjacent said measuring channel, extending substantially parallel to a bottom of said measuring channel and in line with an optical beam passing through said measuring channel and being there placed adjacent an outer edge of said measuring channel;
   (f) said measuring channel having the form of a recess directed at measuring along a flowing direction of said fluid and in a direction substantially perpendicular to a beam path through said channel, said measuring channel having a depth which is less than a distance between said sides of said measuring channel;
   (g) all junctions between surfaces of mutually different extension at and in the vicinity of said measuring channel being gently rounded; and,
   (h) optics adjacent said optical channel having a surface aligned with said channel sides, optical components being provided between said light channels and said channel sides.

2. A measuring head according to claim 1, wherein said width of said measuring channel between channel edges is between 1 and 5 mm.

3. A measuring head according to claim 1, wherein said measuring channel has a depth such that there is negligible friction between a flowing suspension and said bottom of said measuring channel.

4. A measuring head according to claim 1, wherein said measuring channel has the form of an elongated deepening in a measurement indicating body intended for immersion in a suspension on which measurements are to be made.

5. A measuring head according to claim 1, wherein said measuring channel comprises a deepening in a part of an inner wall of a tube through which the suspension flows, said deepening being directed along said tube having said beam path traversing said channel in a direction substantially perpendicular to a direction of said tube.

6. A measuring head according to claim 1, wherein multiple radiation paths with mutually different properties of the radiation transmitted and captured through the suspension via the measuring channel are disposed adjacent one another in the flow direction of said suspension.

7. A measuring head according to claim 6, wherein said multiple radiation paths are formed with the aid of fiber-optic cables or bundles having multiple optic-fiber light guides.

8. Apparatus for preventing blockage of a measuring head for effecting measurements regarding concentration of substances suspended in a flowing medium, said measuring head comprising:
   (a) an open measuring channel which has two mutually opposing channel sides;
   (b) at least one measuring beam transmitted from one side of said channel from a beam source of substantially constant and predetermined intensity during a measuring process;
   (c) radiation indication means for indicating an intensity of the beam transmitted through said medium and received at the other side of said channel, and in which an electric output signal of said radiation indication means is supplied for evaluation to a signal processing device;
   (d) a thin transmitting light channel such as a fiber-optic light guide or a narrow straight channel having a size substantially of the order of said fiber-optic light guide, which transfers a narrow beam for transmitting said measuring beam from said beam to said one channel side, and a thin receiving light channel for transmitting said measuring beam from said other channel side to said radiation indicator;
   (e) said light channels, adjacent said measuring channel, extending substantially parallel to a bottom of said measuring channel and in line with an optical beam passing through said measuring channel and being there placed adjacent an outer edge of said measuring channel;
   (f) said measuring channel having the form of a recess directed at measuring along a flowing direction of said fluid and in a direction substantially perpendicular to a beam path through said channel, said measuring channel having a depth which is less than a distance between said sides of said measuring channel;
   (g) all junctions between surfaces of mutually different extension at and in the vicinity of said measuring channel being gently rounded;
   (h) optics adjacent said optical channel having a surface aligned with said channel sides, optical components being provided between said light channels and said channel sides; and,
   (i) a cleaning arrangement being arranged in connection with said measuring channel and being automatically controlled to effect intermittent mechanical cleaning of said measuring channel, said cleaning arrangement including a brush which when inoperative is held withdrawn in a channel having an opening to a bottom of said measuring channel and which, when operative during said intermittent cleaning of said measuring channels, moves reciprocatingly through said opening.

9. A measuring head according to claim 8, wherein said cleaning arrangement includes a channel through which a flushing or rinsing medium is fed through an opening to said bottom of said measuring channel.

10. Apparatus for preventing blockage of a measuring head for effecting measurements regarding concentration of substances suspended in a flowing medium, said measuring head comprising:
   (a) an open measuring channel which has two mutually opposing channel sides;
   (b) at least one measuring beam transmitted from one side of said channel from a beam source of substantially constant and predetermined intensity during a measuring process;
   (c) radiation indication means for indicating an intensity of the beam transmitted through said medium and received at the other side of said channel, and in which an electric output signal of said radiation indication means is supplied for evaluation to a signal processing device;
   (d) a thin transmitting light channel, such as a fiber-optic light guide or a narrow straight channel having a size substantially of the same order of said fiber-optic light guide, which transfers a narrow beam, for transmitting said measuring beam from said beam source to said one channel side, and a thin receiving light channel for transmitting said measuring beam from said other channel side to said radiation indicator;
   (e) said light channels, adjacent said measuring channel, extending substantially parallel to a bottom of said measuring channel and in line with an optical beam passing through said measuring channel and being there placed adjacent an outer edge of said measuring channel;
   (f) said measuring channel having the form of a recess directed at measuring along a flowing direction of said fluid and in a direction substantially perpendicular to a beam path through said channel, said measuring channel having a depth which is less than a distance between said channel sides of said measuring channel;
   (g) all junctions between surfaces of mutually different extension at and in the vicinity of said measuring channel being gently rounded;
   (h) optical components being provided between said light channels and said channel sides;
   (i) an extreme value of an alternating electrical signal obtained from the radiation detector during measurement on a fluid medium having the same conditions during the measurement being indicated within a predetermined time interval; and,
   (j) the extreme value within each time interval constituting a starting value from which at least one preselected property of said suspension is calculated.

11. A measuring head according to claim 10, wherein said extreme value is a peak value ($V_2$) of the alternating signal during said time interval, and a fine fraction of said suspension is indicated by setting said peak value in relation to a voltage level ($V_0$) obtained by effecting measurements on clear water.

12. A measuring head according to claim 10, wherein said extreme value is a peak value ($V_2$) of the signal, a mean value ($V_{DC}$) of said signal is indicated during said interval, and a coarse fraction of said suspension is indicated by setting said peak value in relation to said mean value of said signal.

13. A method for registering a state of a moving suspension containing particle fractions of mutually very different sizes, comprising illuminating the suspension with a beam of light and detecting light exiting from the suspension for the purpose of producing an electric signal which corresponds to the intensity of the detected light, said method further comprising the steps of:
 (a) illuminating said suspension with the aid of a beam of light which is narrow in relation to interspaces between large particles and detecting light exiting from said suspension within a narrow angular range;
 (b) indicating an extreme value of said electrical signal within predetermined time intervals; and
 (c) forming starting values within each extreme value time interval for the purpose of calculating at least one of the following properties of the suspension:
  (i) concentration of fine fraction or light absorbing substances where, when said extreme value is a peak value ($V_P$), said peak value is placed in relation to a voltage level ($V_O$) obtained by measuring clear water, and when said extreme value is a bottom value, said bottom value is placed in relation to a zero level of said signal;
  (ii) concentration of coarse fraction of said suspension indicated by placing said peak value ($V_P$) in relation to a mean value ($V_{DC}$) of said signal; and,
  (iii) total concentration of suspended substances by addition of (i) and (ii).

14. A method according to claim 13, when indicating light transmitted through the suspension, wherein said extreme value is a peak value ($V_P$) of said signal during said time interval, said mean value ($V_{DC}$) of said signal is indicated, and a coarse fraction of said suspension is indicated by placing said peak value in relation to said mean value of said signal.

15. A method according to claim 13, wherein a fine-fraction concentration is indicated by forming the signal $a*\ln(V_O/V_P)$, where a is a constant obtained by calibration against a suspension having a known fine-fraction concentration.

16. A method according to claim 13, wherein a coarse-fraction concentration is indicated by forming the signal $b*\ln(V_A/V_{DC})$, where b is a constant obtained by calibration against a suspension having a known coarse-fraction concentration.

17. A method according to claim 13, wherein the total concentration of substances suspended in said suspension is indicated by forming the signal $$conc = (\ln(V_O/V_P) + c_1 * \ln((V_P/V_{DC}) * c_2$$

where the constant $c_1$ is a sensitivity coefficient of said measuring apparatus, and $c_2$ is a constant for converting measurement values to concentrations in mg/l, the constants being obtained by calibration against suspensions having known fractions.

18. Apparatus for registering the state of a moving suspension containing fractions having particles of mutually very different sizes, said apparatus including a light source which is operative to illuminate said suspension with a beam of light which is narrow in relation to interspaces between large particles in said suspension, and which further includes a light detector operative to detect light exiting from said suspension within a narrow angular range and also operative to produce an electric signal corresponding to an intensity of light detected, said apparatus comprising a signal processing arrangement which is operative to indicate an extreme value of said signal obtained from said light detector within predetermined time intervals, and which is also operative to calculate at least one of the following properties of said suspension:
 (a) concentration of fine fraction or light absorbing substances where, when said extreme value is a peak value ($V_2$), said peak value is placed in relation to a voltage level ($V_O$) obtained by measuring clear water, and when said extreme value is a bottom value, said bottom value is placed in relation to a zero level of said signal;
 (b) concentration of a coarse fraction of said suspension indicated by placing said peak value ($V_P$) in relation to said mean value ($V_{DC}$) of said signal; and,
 (c) total concentration of suspended substances by addition of (a) and (b), at least one preselected property of said suspension on the basis of said extreme value.

19. Apparatus according to claim 18, wherein the signal processing arrangement is also operative to indicate a direct voltage level ($V_{DC}$) above which the detector signal varies and to calculate a value from an algorithm which includes said extreme value and the indicated direct voltage level and adapted to a configuration of a measuring head including said light source and said light detector.

20. Apparatus according to claim 18, wherein said light source and said light detector are provided in a measuring head comprising:
 (a) an open measuring channel which has two mutually opposing channel sides;
 (b) at least one measuring beam transmitted from one side of said channel from a beam source of substantially constant and predetermined intensity during the measuring process;
 (c) radiation indication means for indicating an intensity of the beam transmitted through said medium and received at the other side of said channel, and in which an electric output signal of said radiation indication means is supplied for evaluation to a signal processing device;
 (d) a thin transmitting light channel, such as a fiber-optic straight channel having a size substantially of the order of said fiber-optic light guide, which transfers a narrow beam for transmitting said measuring beam from said beam source to said one channel side, and a thin receiving light channel for transmitting said measuring beam from said other channel side to said radiation indicator;
 (e) said light channels, adjacent said measuring channel extending substantially parallel to a bottom of said measuring channel and in line with an optical beam passing through said measuring channel and being there placed adjacent an outer edge of said measuring channel;
 (f) said measuring channel having the form of a recess directed at measuring along a flowing direction of said fluid and in a direction substantially perpendicular to a beam path through said channel, said measuring channel having a depth which is less than a distance between said channel sides of said measuring channel;

(g) all junctions between surfaces of mutually different extension at and in the vicinity of said measuring channel being gently rounded; and, (h) optical components being provided between said light channels and said channel sides.

21. Apparatus according to claim 20, wherein said width of said measuring channel between said channel edges is between 1 and 5 mm.

22. Apparatus according to claim 20, wherein arranged in connection with said measuring channel is a cleaning arrangement which is automatically controlled to effect intermittent mechanical cleaning of said measuring channel, said cleaning arrangement including a brush which, when operative, is held withdrawn in a channel having an opening to a bottom of said measuring channel and which, when operative during said intermittent cleaning of said channel, is caused to move reciprocatingly through said opening.

23. Apparatus according to claim 20, wherein said cleaning arrangement includes a channel through which a flushing or rinsing medium is fed through an opening to said bottom of said measuring channel.

24. Apparatus according to claim 14, wherein, inwardly of the radiation-conducting elements mounted in connection with said measuring channel, said measuring channel has a depth such that there is negligible friction between the flowing suspension and the bottom of said measuring channel.

25. Apparatus according to claim 20, wherein, inwardly of the radiation-conducting elements mounted in connection with said measuring channels, said measuring channel has a depth such that there is negligible friction between the flowing suspension and the bottom of said measuring channel.

26. A measuring head according to claim 20, wherein said measuring channel comprises a deepening in a part of an inner wall of a tube through which the suspension flows, said deepening being directed along said tube having said beam path traversing said channel in a direction substantially perpendicular to a direction of said tube.

* * * * *